(12) United States Patent
Putrino et al.

(10) Patent No.: US 6,544,169 B2
(45) Date of Patent: Apr. 8, 2003

(54) EYELID RETRACTION DEVICE

(75) Inventors: Charles R. Putrino, Osprey, FL (US); Willet F. Whitmore, III, Sarasota, FL (US); Stephen E. Brauner, Bradenton, FL (US)

(73) Assignee: Barzell Whitmore Maroon Bells, Inc., Sarasota, FL (US)

( * ) Notice: Subject to any disclaimer, the term of this patent is extended or adjusted under 35 U.S.C. 154(b) by 0 days.

(21) Appl. No.: 09/770,664

(22) Filed: Jan. 29, 2001

(65) Prior Publication Data

US 2002/0103421 A1 Aug. 1, 2002

(51) Int. Cl.[7] ................................................. A61B 1/32
(52) U.S. Cl. ........................ 600/236; 600/219; 600/210
(58) Field of Search ................................. 600/201, 210, 600/219, 235, 236; 604/294

(56) References Cited

U.S. PATENT DOCUMENTS

| | | |
|---|---|---|
| 2,702,540 A | 2/1955 | Debeh |
| 4,085,750 A | 4/1978 | Bosshold |
| 4,321,916 A | 3/1982 | McKee |
| 4,543,096 A | 9/1985 | Keene ........................ 604/300 |
| 4,549,539 A | 10/1985 | Donaldson |
| 4,973,322 A | 11/1990 | Jewart ........................ 604/300 |
| 5,054,906 A | 10/1991 | Lyons, Jr. .................... 351/205 |
| 5,070,860 A | 12/1991 | Grounauer |
| 5,341,798 A | 8/1994 | Grounauer |
| 5,433,190 A | 7/1995 | Sunalp ........................ 600/236 |
| 5,441,040 A | 8/1995 | Williams, Jr. ............... 600/236 |
| 5,618,261 A | 4/1997 | Nevyas ........................ 600/236 |
| 5,946,758 A | 9/1999 | Hohlbein et al. .......... 15/167.1 |
| 6,088,870 A | 7/2000 | Hohlbein .................... 15/167.1 |

*Primary Examiner*—Jeffrey A. Smith
(74) *Attorney, Agent, or Firm*—Pennie & Edmonds, LLP

(57) ABSTRACT

A device is disclosed to retract eyelid by employing the friction and adhesion between the device and the outer surface of the eyelid of an eye without engaging the inside of the eyelid, thus without giving rise to infection, contamination, or injury to the eye. The device comprises a pair of arms joined at a joint. The arms are in a wishbone form with a size and configuration that accommodate the anatomy of the eye. The arms can be embodied in several preferred ways so that the size and configuration of the wishbone can be changed dynamically, adjusted resiliently, or fixed manually. The device is efficient enough to assist an eye care clinician to gain greater access to the exposed surface of an eyeball during an eye care procedure and is simple enough to aid contact lens patients in the process of inserting or removing contact lenses.

26 Claims, 14 Drawing Sheets

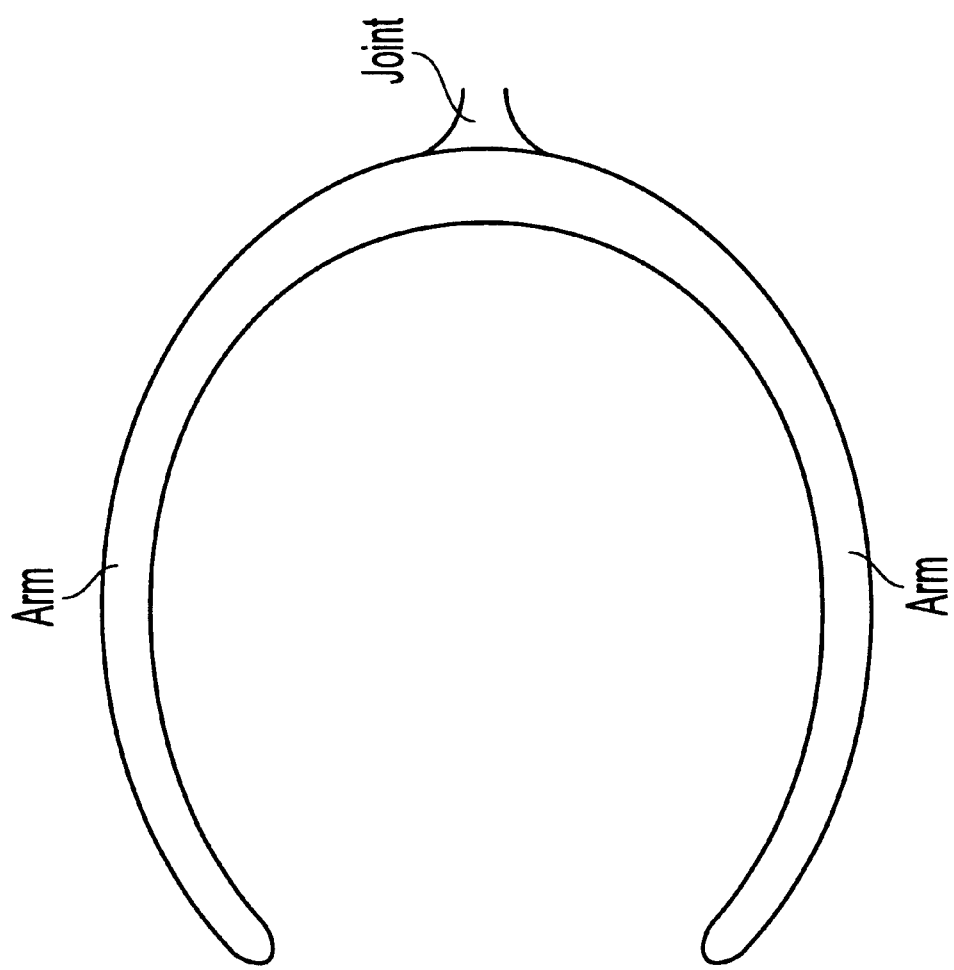

EYELID RETRACTION DEVICE

FIELD OF THE INVENTION

The present invention relates to a device for use in retracting an eyelid to expose an eyeball. Particularly, the present invention relates to a device that exposes an eyeball to allow greater access to the exposed surface of the eyeball during eye examination, surgery, or contact lens insertion and removal.

BACKGROUND

There are many eyelid retracting devices commercially available.

Additionally, many eyelid retracting devices are described in the prior art. In U.S. Pat. No. 5,433,190 to Sunalp, an eyelid speculum device is disclosed. It is used to hold a person's eyelids open for ocular surgery, treatment, examination, or some other reason. It may be inserted between the upper and lower eyelids of a person's eye. In U.S. Pat. No. 5,618,261 to Nevyas, an eye proptosing speculum that applies pressure to urge the eyeball outwardly is disclosed. The speculum includes a pair of blades and a pair of pressors. Each blade is shaped to engage a patient between one of the eyelids and the eyeball.

None of the prior art devices retracts the eyelid without having to engage the mucous membranes (moist) surfaces of the eyelid. Specifically, the prior art devices fit inside the eyelid edges and pull the eyelids back and away from the eyeball to provide access. There exists a safety concern and a need of having an eyelid retracting device that can be used without having to engage the inside of the eyelid and without risking infection, contamination, or injury to the eye.

In addition, the prior art devices are for use in performing eye surgical procedures that require prolonged eyelid retraction. These devices are complicated and cumbersome to use, even by trained healthcare professionals. Another disadvantage of these devices is that they are not disposable, single use designs. Because of reuses and the membrane contact, there is a risk of contamination from patient to patient. Although sterilization between uses minimizes this risk, sterilization results in considerable out-of-service time for the device. For diagnostic and therapeutic procedures that require quick and temporary eyelid separation, it would be advantageous to have an eyelid retracting device that is simple, easy to use, and efficient.

Within the contact lens industry, there is also a need for a simple and safe eyelid retracting device. Many potential contact lens patients desiring to wear contact lenses are unable to do so simply due to their inability to insert or remove the contact lenses. Yet there is currently no eyelid retracting device on the market to assist contact lens patients. A simple and safe eyelid retracting device would help those patients use contact lenses successfully. A simple and safe eyelid retracting device is particularly useful for the novice contact lens patients, patients who possess difficulties with fine hand movements, and other patients who desire to streamline the insertion and removal of contact lenses.

SUMMARY OF THE INVENTION

The present invention provides an eyelid retracting device. The device employs the friction or adhesion between the device and the outer surface of the eyelids. There is no engagement between the device and the inside of the eyelids thus use of the device will not give rise to infection, contamination, or injury to the eye. The device is efficient enough to assist an eye care clinician, such as an optometrist, an ophthalmologist, or an ophthalmic or optometric technician, to gain greater access to the exposed surface of an eyeball during an eye care procedure, such as a routine examination, a diagnostic procedure, a therapeutic procedure, or a surgery. At the same time, the device is simple enough to aid contact lens patients in the process of inserting or removing contact lenses.

In a preferred embodiment, the device comprises an upper arm configured and dimensioned to exert force upon the furrow of an upper eyelid, a lower arm configured and dimensioned to exert force upon the furrow of a lower eyelid, and a U-shaped joint connecting resiliently the arms. The arms form the shape of a wishbone. In one preferred embodiment, the wishbone approximates the size and configuration of the orbit of a human eye. In another preferred embodiment, the wishbone approximates the size and configuration of the outline of the exposed part of an eyeball. Also, the side of the arms are configured to contour the facial bones, that form the orbit of an eye, and the shape of the eyeball.

In a preferred embodiment, the arms are configured so that the configuration and size of the wishbone can dynamically change during application to conform the anatomy of the eye. The configuration with such dynamics includes the configuration of flexible arm parts, the configuration of an arm surface that deflects, the configuration of an arm surface that changes its thickness during application, and the configuration of an arm surface that comprises riblets to enable the change of the arm's thickness during application.

In another preferred embodiment according to the present invention, the device comprises a handle, an upper arm operatively associated with the handle and configured and dimensioned to exert force upon the furrow of an upper eyelid, and a lower arm operatively associated with the handle and configured and dimensioned to exert force upon the furrow of a lower eyelid. The handle is shaped as a cylinder and with a texture, preferably a dull stainless steel finish, a roughened surface finish, a brushed finish, a knurled finish, or a molded irregular finish, to allow maximum ease of maneuvering. The portion of the arms that contacts the outer surface of the eyelid is with a coating, preferably a sticky soft rubber coating, to enhance friction. The arms are resiliently connected to the handle and form the shape of a wishbone which approximates the size and configuration of the outline of the exposed part of an eyeball.

In another preferred embodiment, the device comprises a handle, an upper arm operatively associated with the handle and configured and dimensioned to exert force upon the furrow of an upper eyelid, and a lower arm operatively associated with the handle and configured and dimensioned to exert force upon the furrow of a lower eyelid. The handle includes an adjustor comprising a built-in nut at one end of the handle, a knob at the other end of the handle to turn the nut, a socket, to which one end of each the arm is pivotally connected, a bolt with one end threading through the socket into the handle and the other end connected to a connector, a first strut with one end pivotally connected to the connector and the other end pivotally connected to a mid-point of the upper arm, and a second strut with one end pivotally connected to the connector and the other end pivotally connected to a mid-point of the lower arm. The arms form the shape of a wishbone. The adjustor adjusts the size and configuration of the wishbone to approximate the outline of the exposed part of an eyeball.

In yet another preferred embodiment, the device comprises a handle and an applicator. The applicator is a right circular cylinder with an adhesive coating and a curly shaped surface to match the eyeball radius of curvature. In a preferred embodiment, the cylinder is hollow and the handle is shaped to allow for the cylinder to mount on. In another preferred embodiment, the cylinder is a fixed part at one end of the handle.

In still another preferred embodiment, the device comprises a first double backed adhesive strip, one side of which adheres to one finger of a user and the other side of which applies to the outer surface of the upper eyelid, and a second double backed adhesive strip, one side of which adheres to another finger of a user and the other side of which applies to the outer surface of the lower eyelid. In a preferred embodiment, the double backed adhesive strips are placed directly on a user's fingers. In another preferred embodiment, the double backed adhesive strips are made into rings that fit over the fingers of a user.

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the invention and in which:

FIG. 3b shows the configuration of a wishbone.

DETAILED DESCRIPTION OF THE PREFERRED EMBODIMENT

The present invention provides a device for use in retracting the eyelids. The device employs the friction or adhesion between the device and the outer surface of the eyelid and retracts the eyelids to expose the eyeball to assist an eye care clinician, such as an optometrist, an ophthalmologist, or an ophthalmic or optometric technician, to gain greater access to the exposed surface of the eyeball during an eye care procedure, such as a routine examination, a diagnostic procedure, a therapeutic procedure, or a surgery.

The device can be used in conjunction with a slit lamp, indirect ophthalmoscope, or other instruments used in eye care procedures. Particularly, the device can be used in the procedures of:

1. tonometry, which is the measurement of intraocular pressure of the eye, used for glaucoma diagnosis and treatment;
2. gonioscopy, which is used to assess the structures of the anterior angle of the eye, utilized for glaucoma diagnosis and treatment;
3. conjunctiva and cornea foreign body removal, which is the extraction of a foreign material from the globe of the eye;
4. contact lens assisted and indirect ophthalmoscopy which is an evaluation of the posterior aspect of the eye; and
5. other eye care procedures.

There is no engagement between the device and the mucous membranes (moist) surfaces of the eyelid. Thus, use of the device does not give rise to infection, contamination, or injury to the eye.

The device can also be used in aiding contact lens patients in the process of inserting or removing contact lenses. Use of the device is simple and requires only one hand.

Therefore, a contact lens patient has one free hand for placement or removal of contact lens. Also, in one embodiment, after being positioned to the outer skin of an eye, the device stays in the position due to the friction and adhesion between the device and the outer skin and due to a self-adjusting spring function of the device. This enables the user to free up both hands after positioning the device in place.

Figure 1:
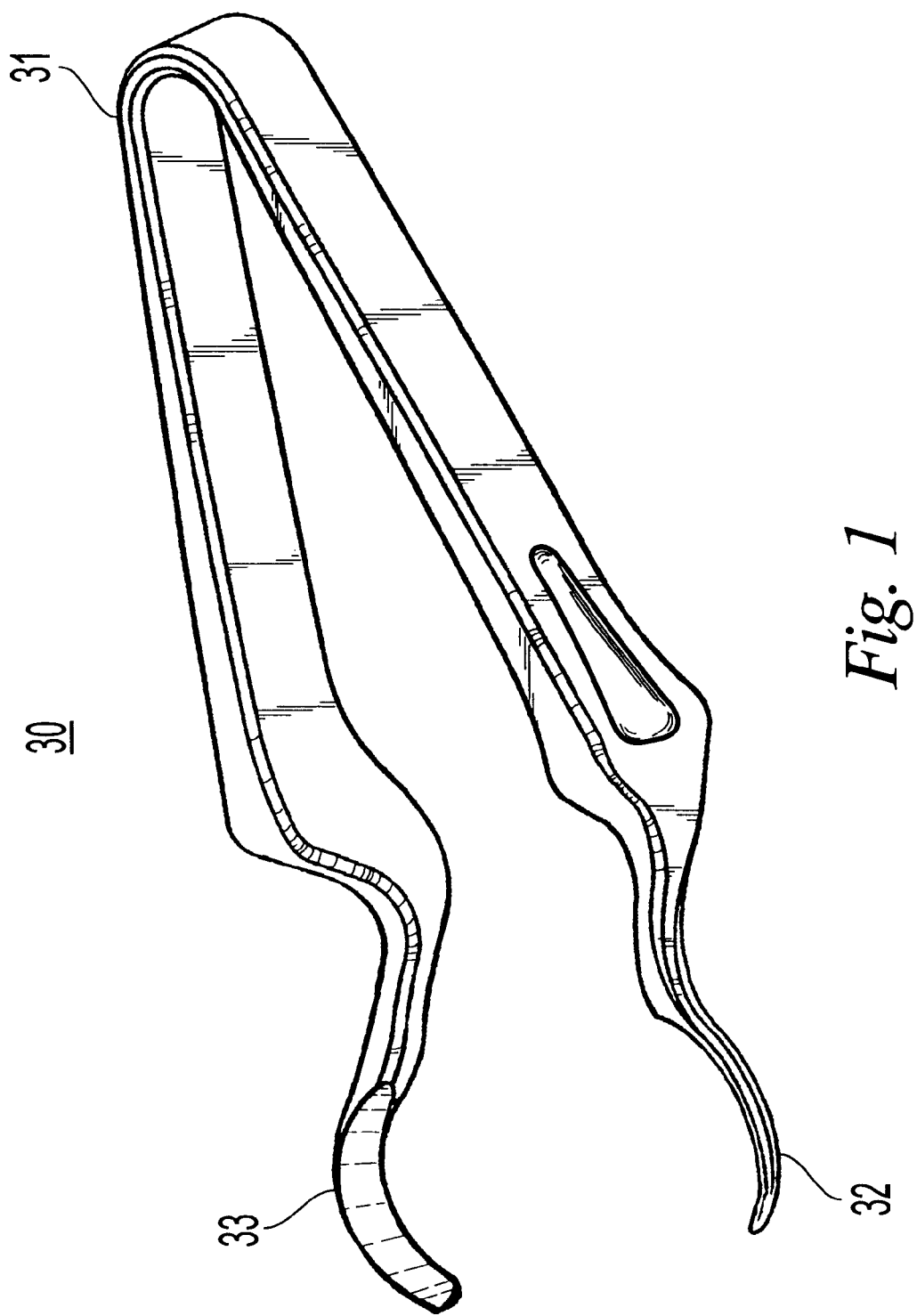
FIG. 1 provides a perspective view of one embodiment of the eyelid retracting device according to the present invention.

FIG. 1 is a perspective depiction of the eyelid retractor according to one embodiment of the present invention. In this embodiment, the eyelid retractor (30) comprises an upper arm (33), a lower arm (32), and a joint (31). The upper arm is configured and dimensioned to accommodate the furrow of an upper eyelid and the lower arm is configured and dimensioned to accommodate the furrow of an lower eyelid. The two arms are so configured and dimensioned such that, when in use, they contact only the outer skin of the eyelid without contacting any mucous membrane or inside of the eye, thus without giving rise to concerns on eye contamination or infection. The two arms are joined at the joint.

The eyelid retractor may be made in different materials. In a preferred embodiment, it is made from plastic. In another preferred embodiment, it is molded. In yet another preferred embodiment, it is made from stainless steel. In still another preferred embodiment, different parts of the device are made from different materials. In still another preferred embodiment, the device are made to be disposable. In still another preferred embodiment, the device are made to be reusable.

Figure 2A:
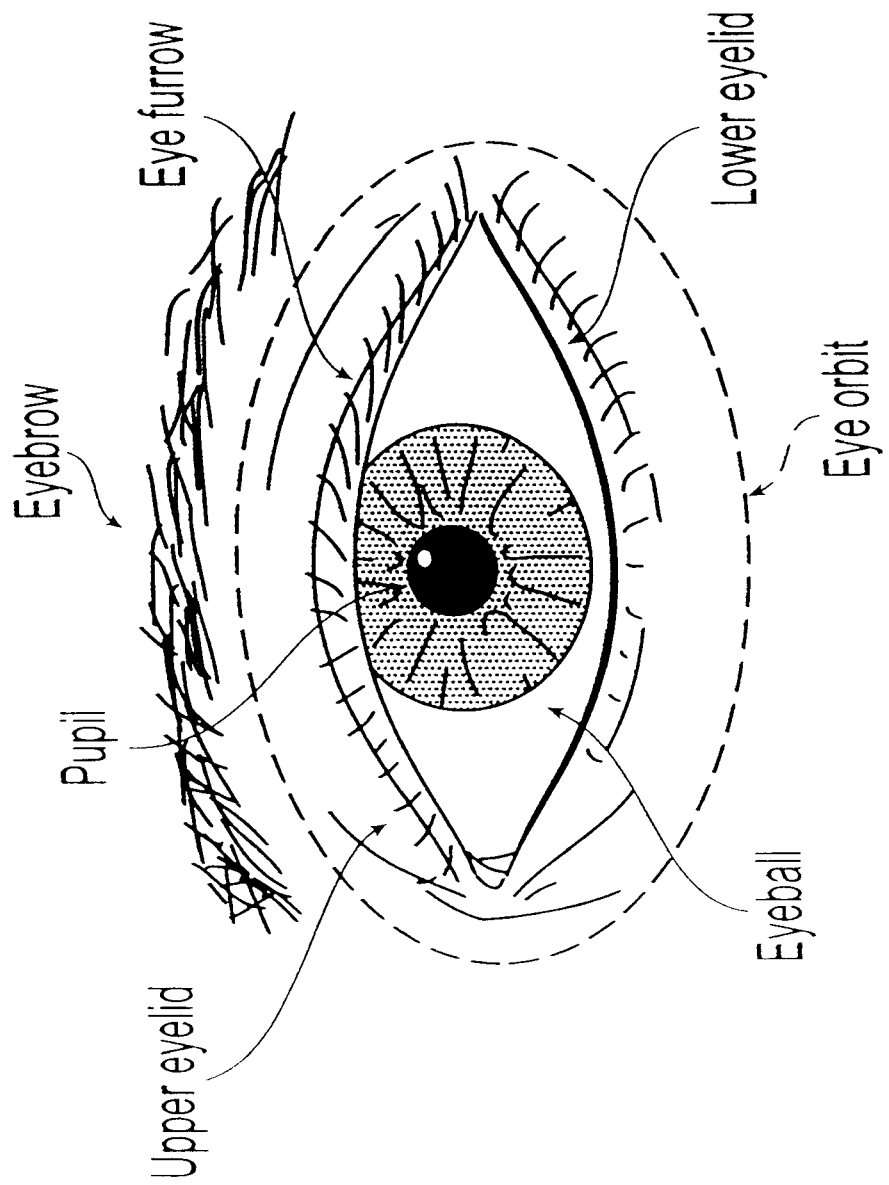
FIG. 2a shows the anatomy of a human eye.

FIG. 2a shows the anatomy of a human eye, with indications of the locations of the upper eyelid, the lower eyelid, the eye furrow, the eyeball, the pupil, the eye orbit, and the eyebrow. As illustrated in FIG. 2a, eyelids are the movable folds that cover the front of the eyeball when closed. They form the outline of the exposed part of the front of the eyeball when open. The upper eyelid is the movable fold above the exposed part of the eyeball and the lower eyelid is the movable fold below the exposed part of the eyeball. An eye furrow is the deep wrinkle of an eyelid. An eye orbit is the bony cavity containing the eyeball.

Figure 2B:
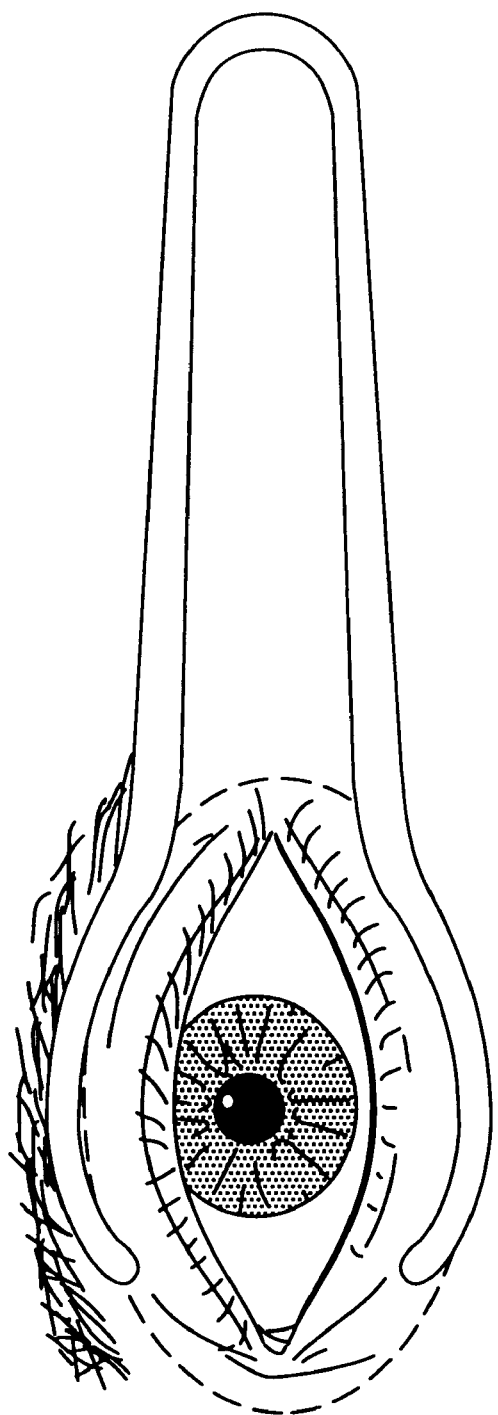
FIG. 2b provides a frontal view of the device of FIG. 1 applied to a human eye.

FIG. 2b shows how the eyelid retractor is applied to an eye when retracting eyelids. The two arms are applied to the outer skins of the eyelids without contacting any mucous membrane inside the eye. The upward movement of the upper arm would retract the upper eyelid upward due to the friction and adhesion between the upper arm and the outer skin of the upper eyelid. Similarly, the downward movement of the lower arm would retract the lower eyelid downward due to the friction and adhesion between the lower arm and the outer skin of the lower eyelid. These movements achieve the retraction of the eyelids.

When the need arises that retraction is desired for only one eyelid, the upper eyelid or the low eyelid, only one arm of the device, the upper arm or the lower arm, may be applied to the eyelid that is in need of retraction.

Figure 3A:
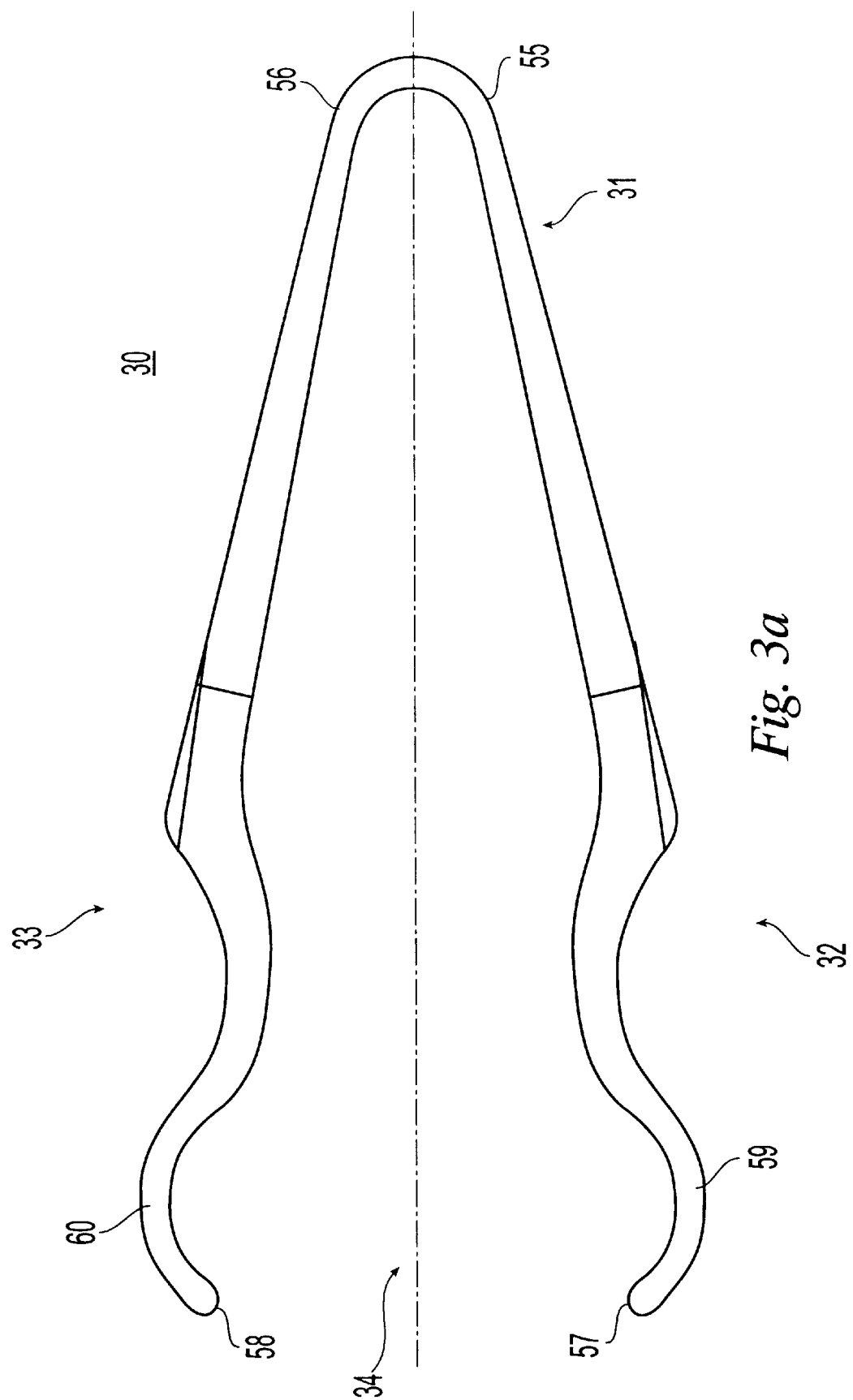
FIG. 3a provides a frontal view of the device of FIG. 1.

FIG. 3a is a frontal view of the eyelid retractor (30) of FIG. 1. Preferably, the joint (31) takes the form of a U-shape. It can also be in a V-shape or some other shape. The arms (32) (33) enclose a space (34). The arms (32) (33) have respective first ends (55), (56) and respective second ends (57), (58). The arms (32) (33) have respective portions (59), (60) that are each spaced apart from the second end of the arm. The portions (59), (60) are arcuate. In a preferred embodiment, the two arms (32) (33) are resiliently joined at the joint (31), such that the arms possess a self-adjusting function and the size and configuration of the enclosed space (34) are changeable, due to the resilience, when the arms are under pressure or squeezing.

In a preferred embodiment, the two arms form the shape of a wishbone. The wishbone referred to here is illustrated in FIG. 3b. As shown in FIG. 3b, a wishbone consists of two substantially similar arms. The two arms are arcuate, each having two ends. The first ends of the arms are joined at a joint and the second ends are free ends. They generally form a U-shape, with the free ends curving more toward each other.

In the preferred embodiment, the wishbone approximates the size and configuration of the outline of the exposed part of an eyeball. When the eyelid retractor is applied to the eye and the arms are in contact with the outer skins of the eyelids, it is pressed inward against the eyeball. The wishbone expands because of the resilience at the joint and it expands to confirm with the size and configuration of the orbit of the eye due to the contour of the eyeball, resulting in the retraction of the eyelids due to the friction and adhesion between the arms and the outer skins of the eyelids.

Alternatively, the wishbone approximates the size and configuration of the orbit of an eye. Before the eyelid retractor is applied to the eye, the arms are squeezed toward each other by a pressure applied to the parts of the arms near the joint. When so squeezed, the arms will move toward each other due to the resilience at the joint and the space enclosed between the arms will be smaller. In use, the arms are squeezed to a degree where the squeezed wishbone approximates the configuration and size of the outline of the exposed part of the eyeball. After eyelid retractor is applied to the eye and the arms are in contact with the outer skins of the eyelids, the squeezing is released and the arms resiliently return to their natural state of wishbone form which confirms with the size and configuration of the orbit of the eye, resulting in the retraction of the eyelids due to the friction and adhesion between the arms and the outer skins of the eyelids. In this embodiment, after being positioned to the outer skins of an eyelids, the device stays in the position due to the friction and adhesion between the device and the outer skin and due to a self-adjusting spring function of the device. This enables the user to free up both hands after positioning the device in place.

Figure 4A:
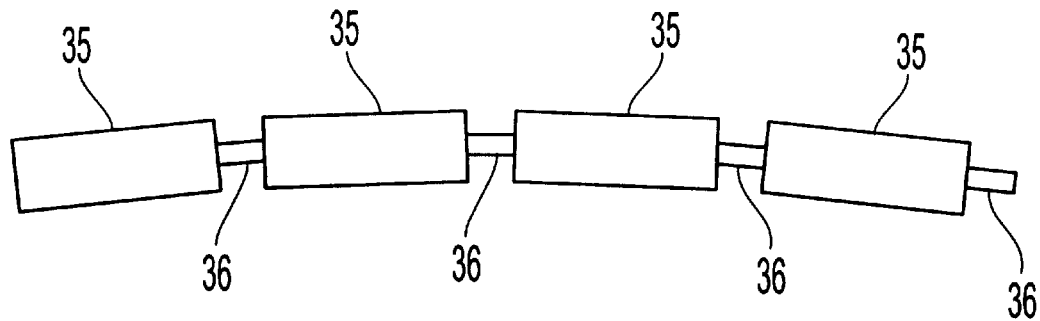
FIGS. 4a–4d show four dynamic configurations of an arm usable with the device of FIG. 1.

In another preferred embodiment, the arms are configured to dynamically change the size and configuration of the wishbone when applied against the eye. In one such preferred embodiment, as shown in FIG. 4a, the portion of the upper arm that contacts the eye skin comprises a plurality of pieces (35) along the length of the arm. Neighboring pieces are bridged together by a soft, thin connector (36). Similarly, the portion of the lower arm (not shown) that contacts the eye skin comprises a plurality of pieces along the length of the arm. Neighboring pieces are bridged together by a soft, thin connector. When unstressed, the pieces are biased to assume a wishbone with a size and configuration conforming those of the outline of the exposed part of an eyeball. When applied to and pressed against the eye, the pieces of the arms flex, changing the size and configuration of the wishbone to conform those of the orbit of the eye, retracting the eyelids due to the friction and adhesion between the pieces of the arms and the outer skins of the eyelids. U.S. Pat. No. 5,946,758 discloses a configuration which dynamically changes its size and configuration to conform those of an object. The references of this patent are expressly incorporated herein.

Figure 4B:
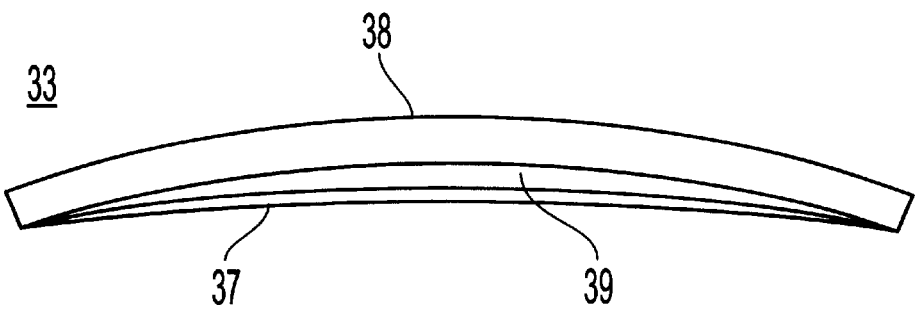

In another preferred embodiment with such a dynamic configuration, as shown in FIG. 4b, the portion of the upper arm comprises a flexible contact face (37) and a rigid backing member (38). In use, the flexible contact face will be in contact with the outer skin of the upper eyelid of an eye and the rigid backing member will not. The rigid backing member and the flexible contact face are made from different materials. The rigid backing member has a peripheral frame or rigid periphery, which defines an elongated opening or aperture, along the length of the arm, configured and dimensioned to accommodate the upper furrow of the eye. The flexible contact face is a flexible layer mounted on the rigid backing member. A space (39) exists within the enclosure of the flexible contact face and the rigid backing member to allow for deflection of the flexible contact face. Similarly, the portion of the lower arm (not shown) comprises a flexible contact face and a rigid backing member. In use, the flexible contact face will be in contact with the outer skin of the lower eyelid of an eye and the rigid backing member will not. The rigid backing member has a peripheral frame or rigid periphery, which defines an elongated opening or aperture, along the length of the arm, configured and dimensioned to accommodate the lower furrow of the eye. The flexible contact face is a flexible layer mounted on the rigid backing member. A space exists within the enclosure of the flexible contact face and the rigid backing member to allow for deflection of the flexible contact face. The size and the configuration of the wishbone formed by the rigid backing members conform those of the orbit of the eyeball.

The flexible contact faces, when unstressed, are biased to assume a wishbone with a size and configuration conforming those of the outline of the exposed part of the eyeball. The difference between the sizes and configurations of the two wishbones is possible because of the existence of the spaces (39). When applied to and pressed against the eye, the flexible contact faces deflect into the spaces (39) and deform against the rigid backing members, changing the size and configuration of the wishbone formed by the flexible contact faces to conform those of the orbit of the eye, retracting the eyelids due to the friction and adhesion between the arms and the outer skins of the eyelids. U.S. Pat. No. 6,088,870 discloses a configuration which dynamically changes to conform the configuration and size of an object. The references of this patent are expressly incorporated herein.

Figure 4C:
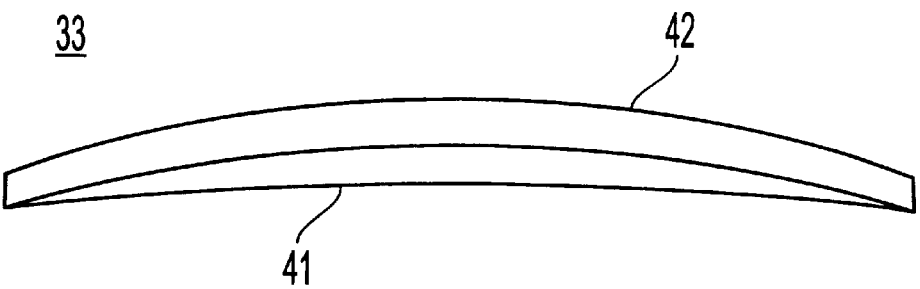

In still another preferred embodiment with such a dynamic configuration, as shown in FIG. 4c, the portion of the upper arm comprises a flexible contact face (41) and a rigid backing member (42). In use, the flexible contact face will be in contact with the outer skin of the upper eyelid of an eye and the rigid backing member will not. The rigid backing member and the flexible contact face are made from different materials. The rigid backing member has a peripheral frame or rigid periphery configured and dimensioned to accommodate the upper furrow of the eye. The flexible contact face is a soft layer mounted on the rigid backing member. The thickness of the flexible contact face increases toward the center of the aperture and is changeable under pressure. Similarly, the portion of the lower arm comprises a flexible contact face and a rigid backing member. In use, the flexible contact face will be in contact with the outer skin of the lower eyelid of an eye and the rigid backing member will not. The rigid backing member and the flexible contact face are made from different materials. The rigid backing member has a peripheral frame or rigid periphery configured and dimensioned to accommodate the lower furrow of the eye. The flexible contact face is a soft layer mounted on the rigid backing member. The thickness of the flexible contact face increases toward the center of the aperture and is changeable under pressure. The size and the configuration of the wishbone formed by the rigid backing members conform those of the orbit of the eyeball. The flexible contact faces, when unstressed, are biased to assume a wishbone with a size and configuration conforming those of the outline of the exposed part of the eyeball. The difference between the sizes and configurations of the two wishbones is possible because the flexible contact faces have a thickness that increases toward the center of the apertures. When applied to and pressed against the eye, the thickness of the flexible contact faces deform against the rigid backing members, changing the size and configuration of the wishbone formed by the flexible contact faces to conform those of the orbit of the eye, retracting the eyelids due to the friction and adhesion between the arms and the outer skins of the eyelids.

Figure 4D:
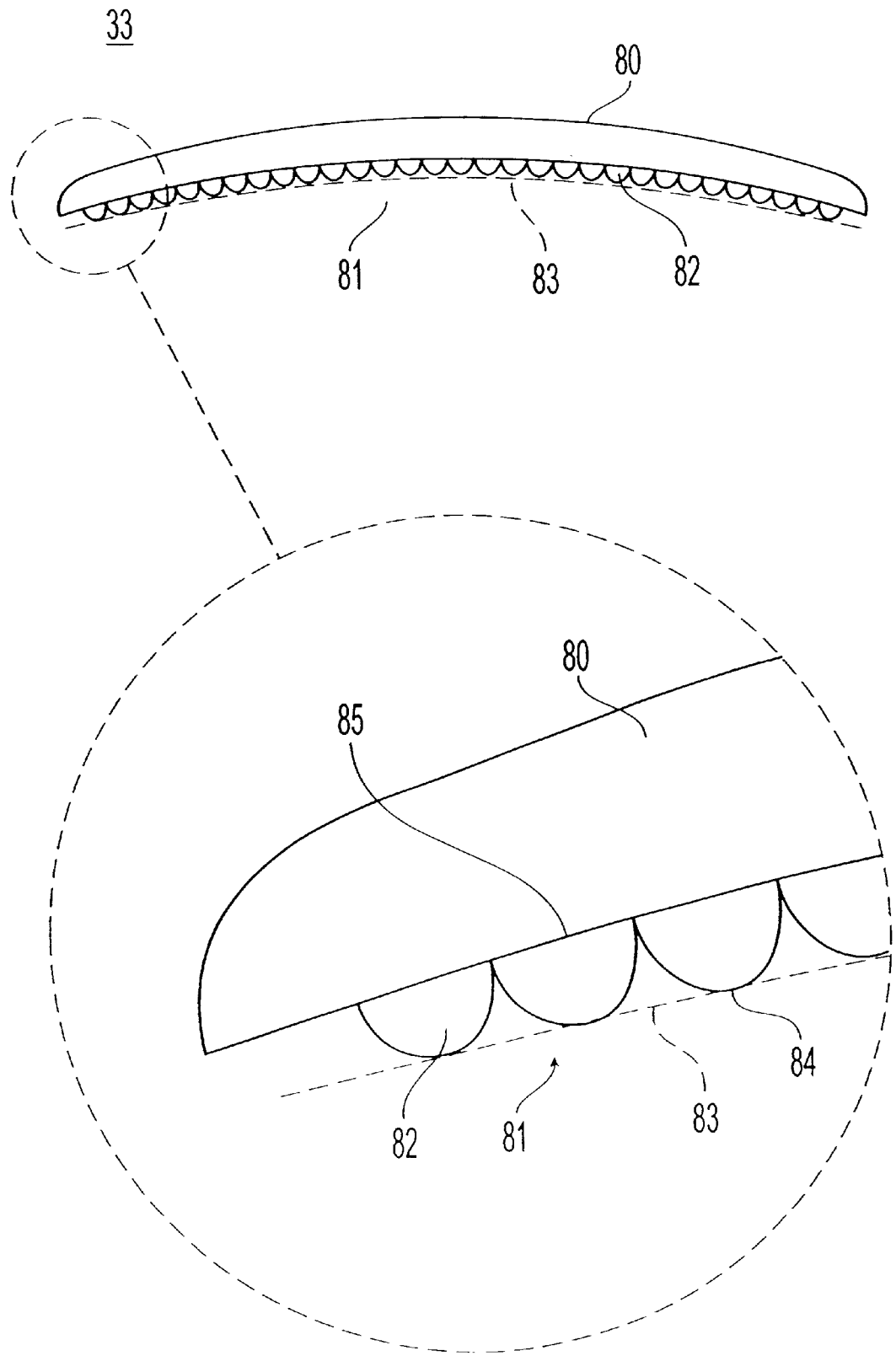

In yet another preferred embodiment with such a dynamic configuration, as shown in FIG. 4d, the portion of the upper arm comprises a flexible contact face (81) and a rigid backing member (80). In use, the flexible contact face will be in contact with the outer skin of the upper eyelid of an eye and the rigid backing member will not. The rigid backing member and the flexible contact face are made from different materials. Preferably, they are made using a two-part injection molding process. The rigid backing member has a peripheral frame or rigid periphery configured and dimensioned to accommodate the upper furrow of the eye. The flexible contact face (81) comprises a plurality of soft riblets (82). The riblets are mounted along the length of the rigid backing member (80), with their bases (85) attached to the rigid backing member and the tips (84) extended away from the rigid backing member. The tips of the riblets form the outline (83) of the flexible contact face (81). The distance between the base (85) and the tip (84) defines a riblet's extension. The extensions of the riblets define the thickness of the flexible contact face. The riblets are made in a way such that the closer the riblet is to the center of the aperture, the thicker its extension is. Therefore, the thickness of the flexible contact face increases toward the center of the aperture. Also, the riblets are made from soft material. Thus the thickness of the flexible contact face is changeable under pressure. Similarly, the portion of the lower arm comprises a flexible contact face and a rigid backing member. In use, the flexible contact face will be in contact with the outer skin of the upper eyelid of an eye and the rigid backing member will not. The rigid backing member and the flexible contact face are made from different materials. Preferably, they are made using a two-part injection molding process. The rigid backing member has a peripheral frame or rigid periphery configured and dimensioned to accommodate the lower furrow of the eye. The flexible contact face comprises a plurality of soft riblets. The riblets are mounted along the length of the rigid backing member, with their bases attached to the rigid backing member and the tips extended away from the rigid backing member. The tips of the riblets form the outline of the flexible contact face. The distance between the base and the tip defines a riblet's extension. The extensions of the riblets define the thickness of the flexible contact face. The riblets are made in a way such that the closer the riblet is to the center of the aperture, the thicker its extension is. Therefore, the thickness of the flexible contact face increases toward the center of the aperture. Also, the riblets are made from soft material. Thus the thickness of the flexible contact face is changeable under pressure. The size and the configuration of the wishbone formed by the rigid backing members conform those of the orbit of the eyeball. The flexible contact faces, when unstressed, are biased to assume a wishbone with a size and configuration conforming those of the outline of the exposed part of the eyeball. The difference between the sizes and configurations of the two wishbones is possible because the flexible contact faces have a thickness that increases toward the center of the apertures. When applied to and pressed against the eye, the riblets flatten and the thickness of the flexible contact faces deform against the rigid backing members, changing the size and configuration of the wishbone formed by the flexible contact faces to conform those of the orbit of the eye, retracting the eyelids due to the friction and adhesion between the arms and the outer skins of the eyelids.

Figure 5:
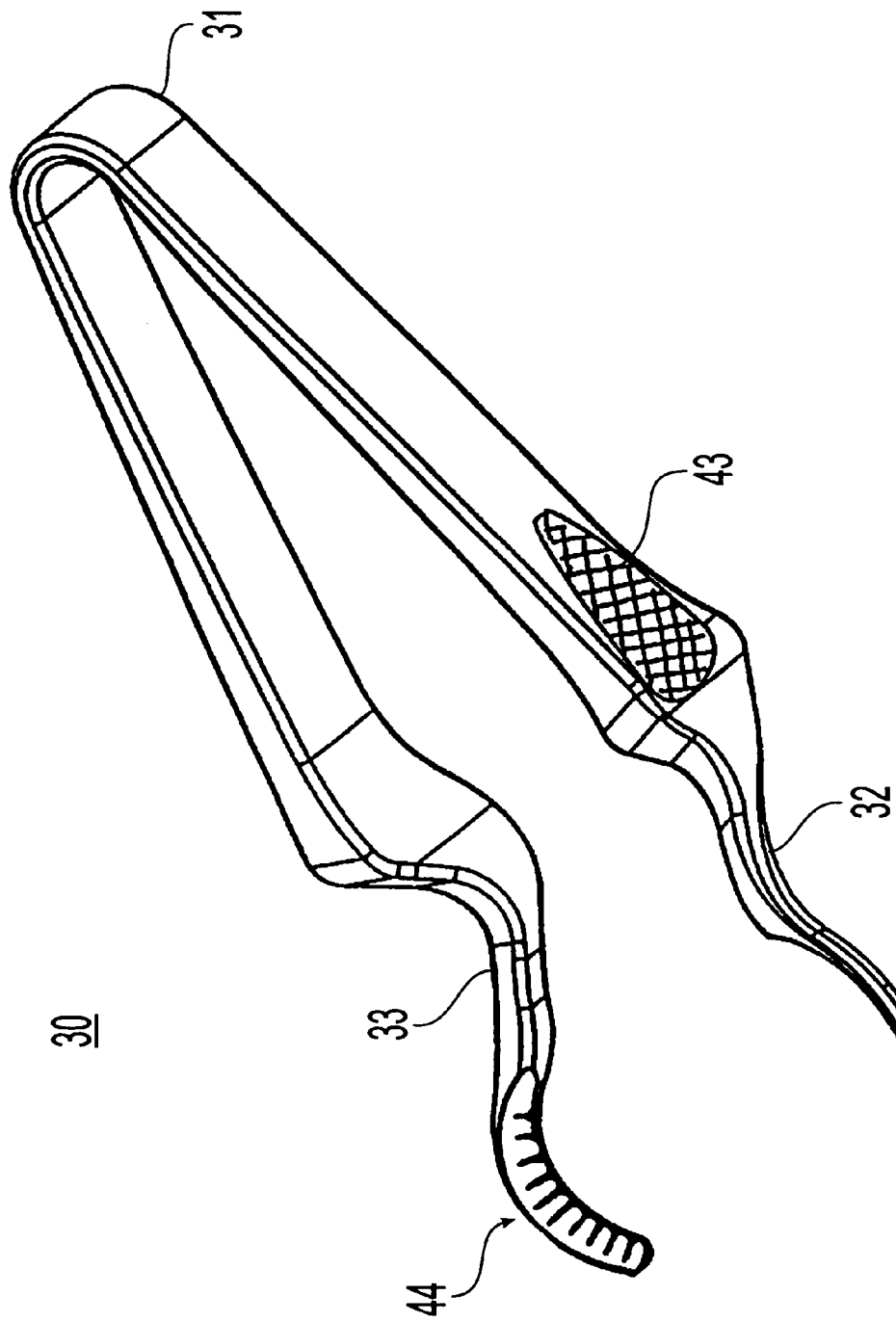
FIG. 5 provides a perspective view of the device of FIG. 1, with arms having a dynamic radius.

FIG. 5 is a perspective view of the device (30) of FIG. 1. It shows that a recess (43) may be made at each side of the device for a user's fingers to achieve maximum ease of maneuvering. In a preferred embodiment, the surfaces of the recesses are with a texture for better handling. Preferably, the texture is a brush finish or a roughened surface finish. Alternatively, the surfaces are molded with a material of adequate roughness. Still alternatively, the surfaces are serrated or grooved.

In another preferred embodiment (not shown in FIG. 5), the portion of the surface at each side the device is with a texture for a user's fingers to achieve maximum ease of maneuvering. Preferably, the texture is a brush finish or a roughened surface finish. Alternatively, the texture is a surface molded with a material of adequate roughness. Still alternatively, the surface is serrated or grooved.

Figure 6:
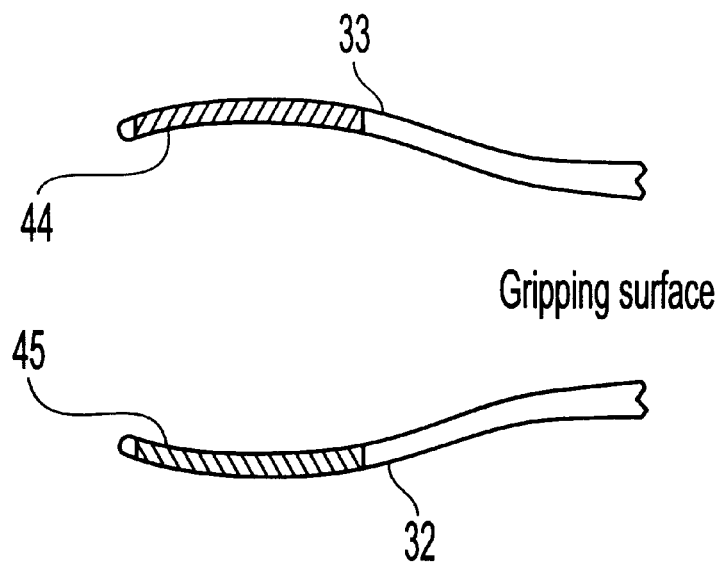
FIG. 6 provides a frontal view of arms usable with the device of FIG. 1.

FIG. 5 also shows that, in a preferred embodiment, deep cuts are made on the parts of the arms (44) that contact the outer skin of the eyelids. These cuts are filled with sticky soft rubber to enhance friction and adhesion between the arms and the eyelids. In another preferred embodiment, the parts of the arms (44) that contact the outer skin of the eyelids are with a coating to enhance friction and adhesion between the arms and the eyelids. Preferably, the coating is sticky soft rubber. In yet another preferred embodiment, as shown in FIG. 6, the parts of the arms (44) that contact the outer skin of the eyelids are serrated or grooved to enhance the friction and adhesion between the arms and the eyelids. In still another preferred embodiment, the parts of the arms (44) that contact the outer skin of the eyelids are with a texture to enhance the friction and adhesion between the arms and the eyelids. Preferably, the texture is a brush finish or a roughened surface finish. Alternatively, the texture is a layer molded with a material of adequate roughness. Still alternatively, the texture is a gripping surface.

Figure 7:
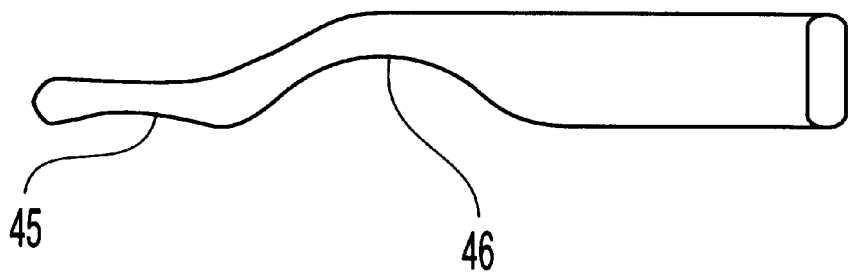
FIG. 7 provides a side view of an arm of the device of FIG. 1, with recesses to facilitate the shape of eyeball and facial bone.

FIG. 7 is a side view of the upper arm (33) of the eyelid retractor (30) of FIG. 1. In FIG. 7, the view of the upper arm is rotated from that shown in FIG. 3*a* such that the anterior of the upper arm in FIG. 3*a* is now the superior of the upper arm in FIG. 7. Likewise, the posterior of the upper arm in FIG. 3a is now the interior of the upper arm. In FIG. 7, the interior part of the upper arm is the part that contacts the upper eyelid of an eye. In a preferred embodiment, a recess (45) is made at the interior of the upper arm to conform with the size and configuration of the eyeball. In another preferred embodiment, a recess (46) is made at the interior of the upper arm to conform with the size and configuration of the facial bone surrounding the eye. In yet another preferred embodiment, both recess (45) and recess (46) are made at the interior of the upper arm to conform, respectively, with the size and configuration of the eyeball and with the size and configuration of the facial bone surrounding the eye. Such configurations are for a better association, and therefore an enhanced adhesion between the eyelid retractor and the eye. They are designed to permit easy manual control and application of the eyelid retractor to the eyelid without interfering with the facial bones that form the orbit of an eye. Similarly, in a preferred embodiment, at the part of the lower arm (not shown) that contacts the lower eyelid of an eye, a recess is made to conform with the size and configuration of the eyeball.

In another preferred embodiment, a recess is also made to conform with the size and configuration of the facial bone surrounding the eye. In yet another preferred embodiment, both recesses are made to conform to conform, respectively, with the size and configuration of the eyeball and with the size and configuration of the facial surrounding the eye.

Figure 8:
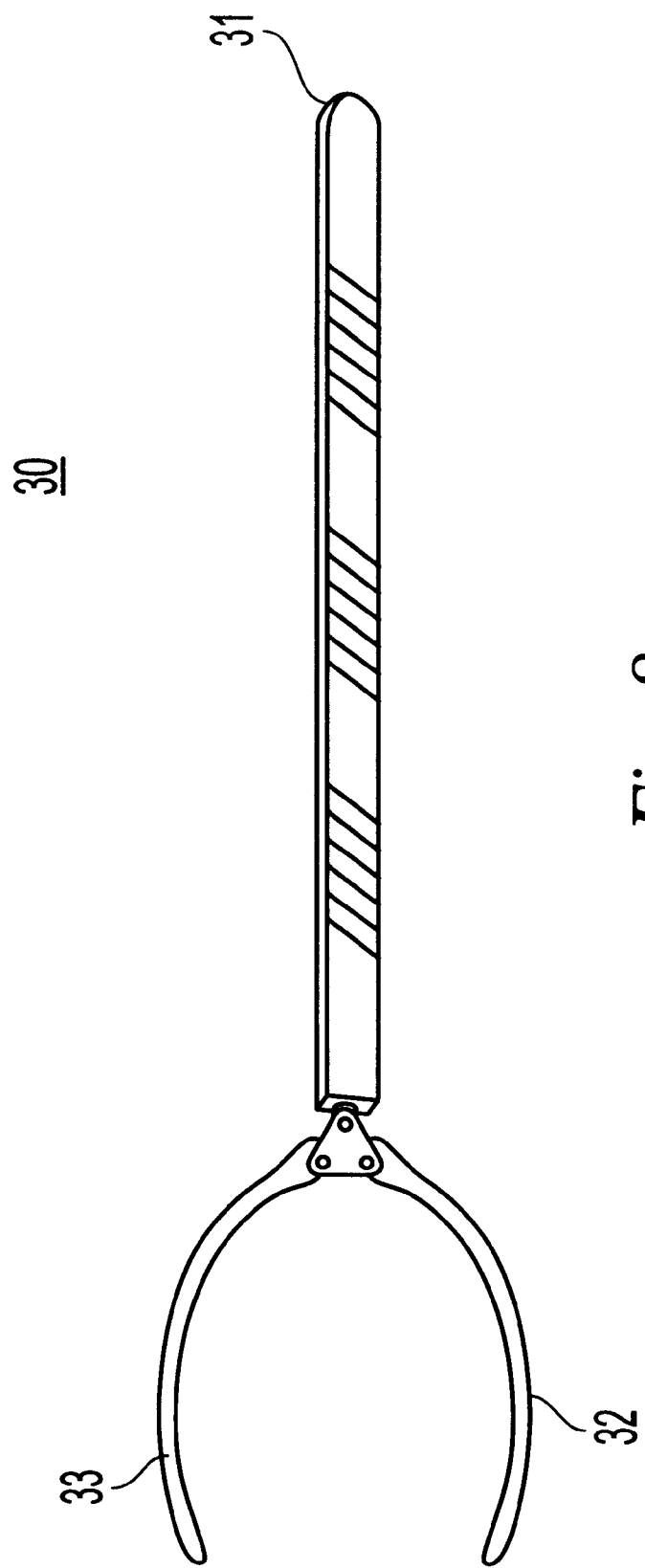
FIG. 8 provides a frontal view of another embodiment of the eyelid retracting device according to the present invention.

FIG. 8 shows another preferred embodiment of the eyelid retractor according to the present invention. In FIG. 8, the joint (31) of the eyelid retractor (30) is in the form of a handle. The upper arm (33) and the lower arm (32) are joined at one end of the handle. The body of the handle is for manipulation of the device. The handle has a width sized to maximize precision of handling. Flats may be included on the surface of the handle for locating fingers. In a preferred embodiment, the handle is shaped as a elongated cylinder. Preferably, the surface of the handle is with a texture for ease of maneuvering. The texture is preferably dull stainless steel finish. Alternatively, the texture is roughened surface finish. Still alternatively, the texture is brushed finish. Yet still alternatively, the texture is knurled finish. The arms (32) (33) are in the form of a wishbone shape. In use, the device (30) is placed along the outline of the exposed part of the eyeball. Specifically, the device (30) is placed on the outer surface and within the furrows of the eyelids. Pressure would be placed on the device (30) against the eyelids and adjacent anatomy. As the device (30) is pressed inward the bony cavity of the eye anatomy, the arms (32) (33) open up because of the spherical shape of the eyeball. Specifically, the arms (32) (33) open up because the cross-section area of the eyeball increases as the device (30) is pressed inward. The arms (32) (33) are able to open up because of their resiliency and self-adjusting spring function. When the arms (32) (33) open up, the friction between the arms (32) (33) and the skin of the eyelids retracts the eyelids.

Figure 9:
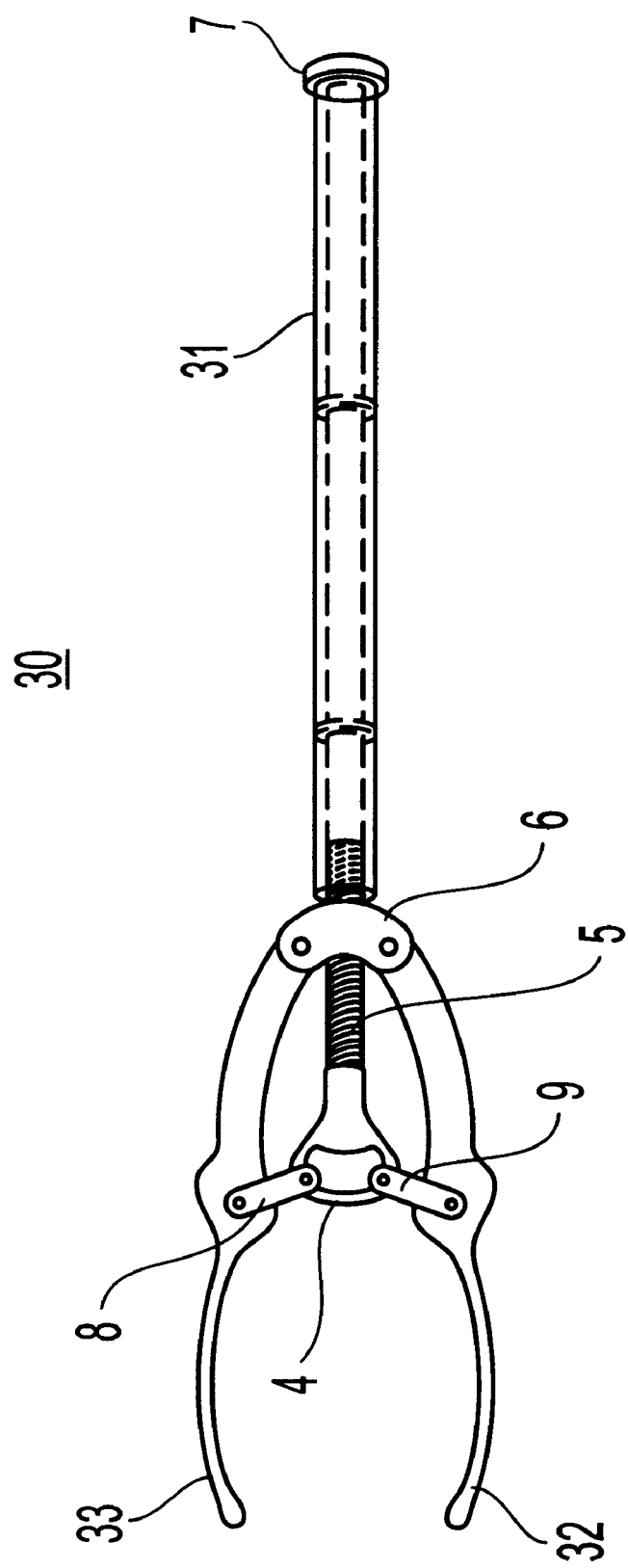
FIG. 9 provides a frontal view of another embodiment of the eyelid retracting device according to the present invention.

FIG. 9 shows a frontal view of another embodiment of the device (30). The device (30) is embodied in a retractable form with movable parts. The retractable form is designed exclusively for the skilled eye care clinician or other appropriately trained health care personnel and is preferably made of non-disposable material, such as stainless steel. The device (30) has a cylindrical handle as the joint (31) and two arms (32) (33). The handle (31) may be made with a special texture to allow for ease of handling. The special texture includes a dull stainless steel finish, a roughened surface finish, a brushed finish, and a knurled finish. The arms (32) (33) are in the form of a wishbone shape. The span between arms (32) (33) is adjustable. One end of each arm is pivotally connected to a socket (6). A mid-point of each arm is also pivotally connected to one end of a connector (4) by way of two struts (8) (9), with each strut pivotally connected (4) to the mid-point of a respective arm. The other end of the connector (4) is connected to a bolt (5). The bolt (5) is threaded, through the socket (6), into the handle (31). The handle (31) is made hollow at one end to allow for the bolt (5) to thread in and to serve as a nut for the bolt. A knob (7) is fixed at the other end of the handle (31). The knob (7) turns to rotate the nut in the handle (31) against the bolt (5), changing the length of the bolt extended to the left from the socket and adjusting the distance between the two arms (32) (33). This adjustment is for the arms (32) (33) to best approximate the size and configuration of the outline of the exposed part of the eyeballs of different users, in recognition that different users may have eyeballs of different sizes.

Figure 10A:
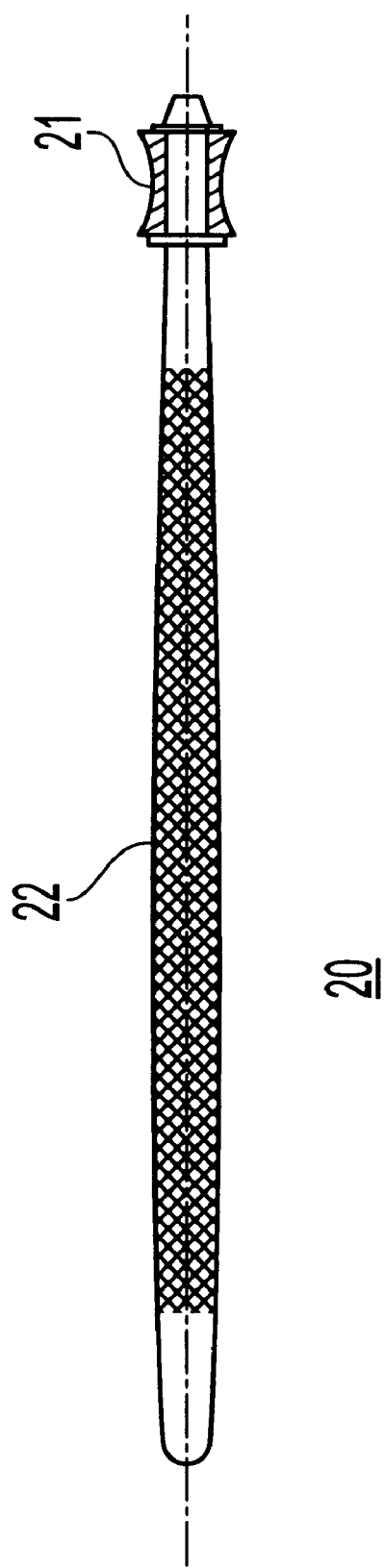
FIG. 10a provides a frontal view of another embodiment of the eyelid retracting device according to the present invention.

FIG. 10*a* shows another embodiment of the eyelid retracting device according to the present invention. The device (20) has an applicator (21) and a handle (22). In a preferred embodiment, the applicator (21) is a right circular cylinder and has a surface with a curly shape to match the eyeball radius of curvature. This embodiment is for the application of the device to one eyelid, the upper or the lower eyelid.

In a preferred embodiment, the applicator (21) has a surface with an adhesive coating allowing for it to stick to the outer surface of an eyelid. Preferably, the coating is sticky soft rubber. The preferable material for the adhesive surface of the applicator (21) is white polycarbonate. In another preferred embodiment, the surface of the applicator is serrated or grooved to enhance the friction and adhesion between the surface of the applicator and the eyelids. In still another preferred embodiment, the applicator is with a texture to enhance the friction and adhesion between the surface of the applicator and the eyelids. Preferably, the texture is a brush finish or a roughened surface finish. Alternatively, the texture is a surface molded with a material of adequate roughness. Still alternatively, the texture is a gripping surface.

In a preferred embodiment, the handle is an elongated cylindrical stem. Preferably, the handle is with a texture. The preferable texture of the handle (22) is a machined surface with a roughness 63 or higher on non-threaded surfaces.

Figure 10B:
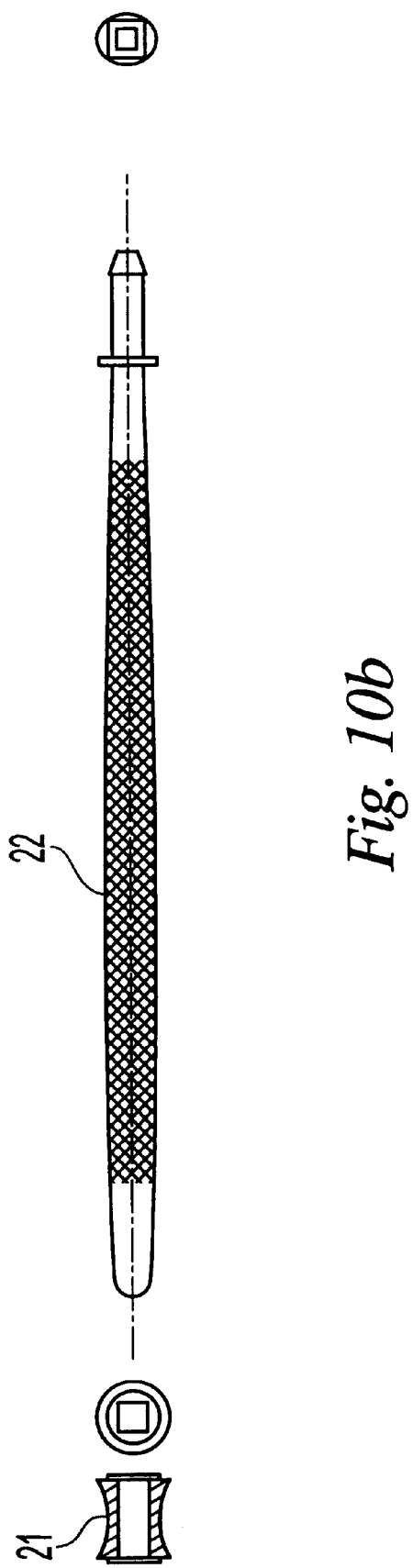
FIG. 10b provides a frontal view of another embodiment of the eyelid retracting device according to the present invention.

The association between the handle and the applicator may be in a variety of ways. In a preferred embodiment shown in FIG. 10*b*, the applicator (21) is hollow and it mounts on and fastens to one end of the handle (22). The applicator (21) may fasten to the handle (22) in different ways. In a preferred embodiment, the applicator (21) snaps on and may rotate around the handle (22). In this way, the handle (22) serves as an axis of the applicator (21). The device (20) would be placed on the outer surface of the eyelid, with the applicator (21) sticking to the outer surface of the eyelid. The handle (22) is moved up, if the device (20) is applied to retract the upper eyelid, or down, if the device (20) is applied to retract the lower eyelid. Such a move of the handle (22) would cause the cylinder (21) to rotate and roll. The rolling action of the cylinder (21), combined with the adhesion between the surface of the applicator (21) and the outer skin of the eyelid, would roll back and retract the eyelid.

In another preferred embodiment, the applicator (21) snaps and tightens on the handle (22). In this way, the cylinder (21) would not rotate around the handle (22). The device (20) is placed on the outer surface of the eyelid, with the applicator (21) sticking to the outer surface of the eyelid. The handle (22) is rolled up, if the device (20) is applied to retract the upper eyelid, or down, if the device (20) is applied to retract the lower eyelid. Such a rolling action of the handle (22) would cause the applicator (21) to roll because the applicator (21) is tightly fastened to the handle (22). The rolling action of the applicator (21), combined with the adhesion between the surface of the applicator (21) and the outer skin of the eyelid, would then roll back and retract the eyelid.

Preferably, the applicator (21) is made of disposable material, such as plastic or molded material, for single use. The handle (22) could be made reusable.

In yet another preferred embodiment, the device (20) is constructed as a single unit, with the applicator (21) being an integral part at one end of the device (20), in a similar way in which the handle and the applicator of a "Q-tip" are constructed. In this case, the whole device (20) is preferably disposable.

Figure 11A:
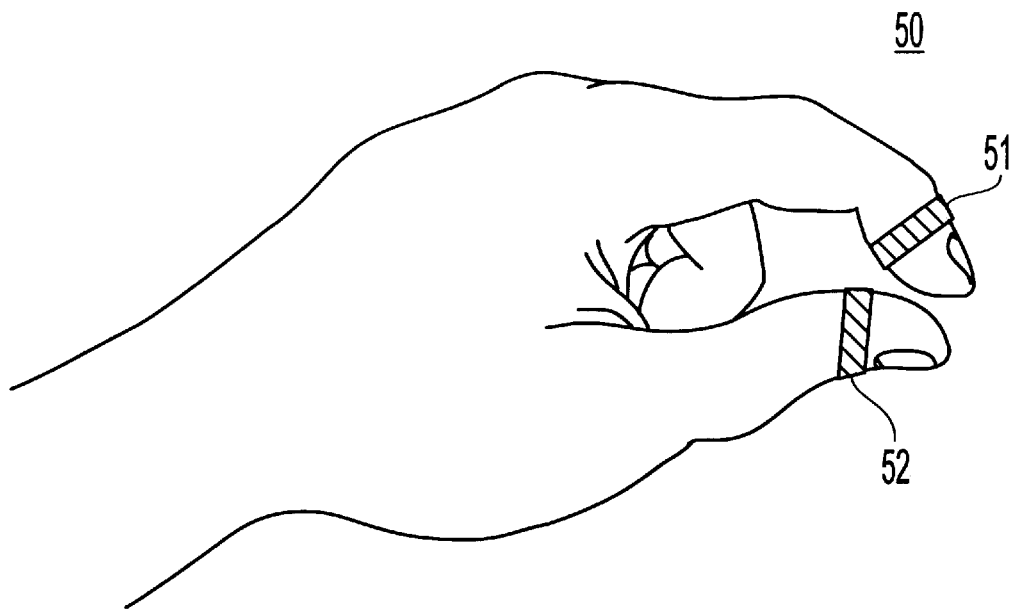
FIG. 11a provides a frontal view of another embodiment of the eyelid retracting device according to the present invention.
Figure 11B:
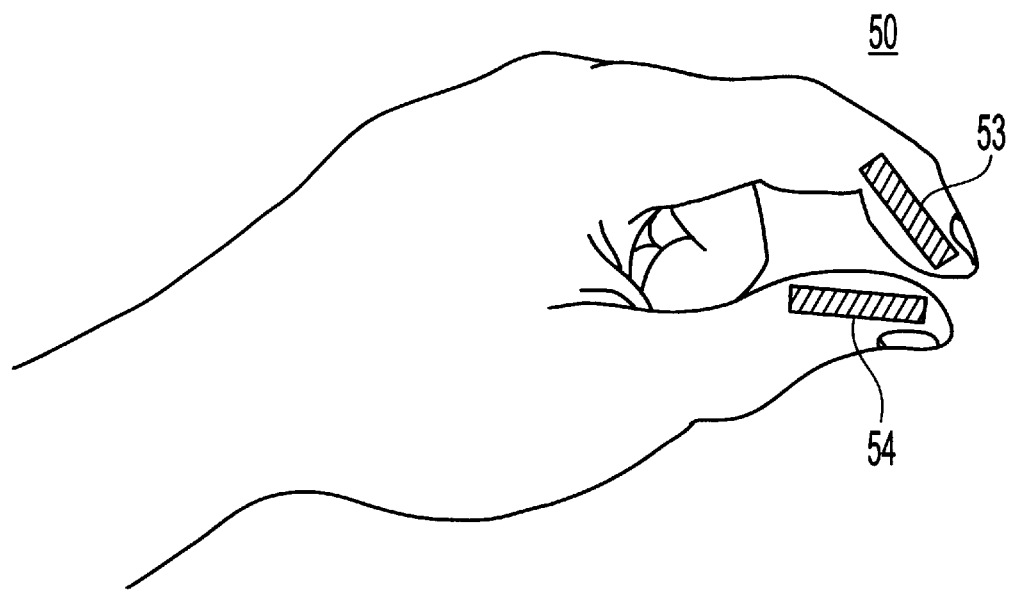
FIG. 11b provides a frontal view of another embodiment of the eyelid retracting device according to the present invention.

FIGS. 11a–b show another embodiment of the eyelid retracting device according to the present invention. In this embodiment, the device (50) comprises double backed adhesive rings (51) (52) to accomplish eyelid retraction. As shown in FIG. 11a, double backed adhesive rings (51) (52) are fit over fingers. One ring would be fit over each of two of a user's fingers. The two fingers would be placed on the outer surface of the eyelids, allowing for one ring to stick to the outer surface of the upper eyelid and the other ring to stick to the outer surface of the lower eyelid. The rings are placed in such area of the fingers as to maximize the maneuvering for the purpose of retracting the eyelids. The user would move, in the upward direction, the finger with the ring attached to the upper eyelid. At the same time, the user may move, in the downward direction, the finger with the ring attached to the lower eyelid. Such motion, combined with the adhesiveness of the rings, would roll back and retract the eyelids.

Preferably, as shown in FIG. 11a, the rings are fit over the thumb and index fingers for ease of maneuvering, because the thumb and the index fingers are likely more capable in accomplishing the eyelid retraction. A user would allow the ring over the index finger to stick to the outer surface of the upper eyelid and the ring over the thumb to stick to the outer surface of the lower eyelid. By moving the index finger upwards and moving the thumb downwards, the rings would roll and retract the eyelids.

When the need arises that retraction is desired for only one eyelid, the upper eyelid or the low eyelid, only one ring of the device may be applied to the eyelid that is in need of retraction.

In another preferred embodiment, as shown in FIG. 11b, the device (50) comprises double backed adhesive strips (53) (54). They are placed on two fingers. That is, one strip is placed on each of two of a user's fingers. The strips are placed in such area of the fingers as to maximize the maneuvering for the purpose of retracting the eyelids. Preferably, the strips are placed on the sides of the fingers which will be in contact with the eyelids, as shown in FIG. 11b. The user would then apply the two fingers to the outer surface of the eyelids, allowing for one strip to stick to the outer surface of the upper eyelid and the other strip to stick to the outer surface of the lower eyelid. The user would move, in the upward direction, the finger with the strip sticking to the upper eyelid. At the same time, the user may move, in the downward direction, the finger with the strip sticking to the lower eyelid. Such motion, combined with the adhesiveness of the strips, would roll back and retract the eyelids.

As shown in FIG. 11b, the strips are preferably placed on the thumb and index fingers for ease of maneuvering. A user would allow the strip on the index finger to stick to the surface of the upper eyelid and the strip on the thumb to stick to the surface of the lower eyelid. By moving the index finger upwards and moving the thumb downwards, he strips would roll and retract the eyelids.

When the need arises that retraction is desired for only one eyelid, the upper eyelid or the low eyelid, only one strip of the device may be applied to the eyelid that is in need of retraction.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below.

What is claimed is:

1. An eyelid retracting device for retracting upper and lower eyelids to expose an eyeball, said device comprising:
   an upper arm having a first end, a second end, and an upper arm arcuate portion, the upper arm arcuate portion being spaced apart from the second end of the upper arm and configured and dimensioned to exert force upon an upper eyelid furrow;
   a lower arm having a first end, a second end, and a lower arm arcuate portion, the lower arm arcuate portion being spaced apart from the second end of the lower arm and configured and dimensioned to exert force upon a lower eyelid furrow; and
   a joint operatively associated with the first ends of the upper and lower arms to provide relative movement between the second ends of the upper and lower arms such that, when the upper and lower arm arcuate portions of the arms are positioned in contact with the respective eyelid furrows and a force is exerted, the eyelid furrows are retracted to expose the eyeball.

2. The eyelid retracting device of claim 1 wherein the upper and lower arm arcuate portions that contact the eyelid furrows have a coating thereupon to enhance friction.

3. The eyelid retracting device of claim 2 wherein said coating is a rubber coating.

4. The eyelid retracting device of claim 1 wherein serrations are made on the upper and lower arm arcuate portions that contact the eyelid furrows to enhance friction.

5. The eyelid retracting device of claim 1 wherein cuts are made on the upper and lower arm arcuate portions that contact the eyelid furrows, said cuts being filled with rubber to enhance friction.

6. The eyelid retracting device of claim 1 wherein said first ends of said arms are resiliently associated with said joint.

7. The eyelid retracting device of claim 1 wherein said arms form a wishbone shape.

8. The eyelid retracting device of claim 7 wherein said wishbone approximates the size and configuration of the exposed part of an eyeball.

9. The eyelid retracting device of claim 8 wherein said size and configuration of said wishbone are changeable under pressure to approximate the size and configuration of a human eye orbit.

10. The eyelid retracting device of claim 7 wherein said wishbone approximates the size and configuration of a human eye orbit.

11. The eyelid retracting device of claim 10 wherein said size and configuration of said wishbone are changeable under squeezing to approximate the size and configuration of the exposed part of an eyeball.

12. The eyelid retracting device of claim 1 wherein said joint is in the form of a U-shape.

13. The eyelid retracting device of claim 1 wherein:
    said upper arm further comprises a first plurality of pieces along the length of said upper arm and a first connector between each pair of neighboring first plurality of pieces of said upper arm; and
    said lower arm further comprises a second plurality of pieces along the length of said lower arm and a second connector between each pair of neighboring second plurality of pieces of said lower arm;
    wherein each piece of a pair of neighboring said pieces are resiliently connected to at least one of said connectors, said upper and lower arms assuming a wishbone shape which approximates the size and configuration of the exposed part of the eyeball when not in contact with the eyelids, but said wishbone shape assuming a size and configuration which conforms to that of a human eye orbit when in contact with the eyelids.

14. The eyelid retracting device of claim 1, wherein said upper and lower arms each further comprising a rigid backing member and a flexible contact face mounted on said rigid backing member to define a space therebetween;
    wherein said rigid backing members assuming a wishbone shape which approximates the size and configuration of a human eye orbit, said flexible contact faces assuming a wishbone shape which approximates the exposed part of an eyeball, said flexible contact faces deforming into the spaces to conform to the size and configuration of the wishbone formed by said rigid backing members when in contact with the eyelid furrows.

15. The eyelid retracting device of claim 1, wherein said upper and lower arms each further comprising a rigid backing member and a flexible contact face mounted on said rigid backing member;
    wherein said rigid backing members assuming a wishbone shape which approximates the size and configuration of a human eye orbit, said flexible contact faces 1assuming a wishbone shape which approximates the exposed part of an eyeball, said flexible contact faces reducing their thickness to conform to the size and configuration of the wishbone formed by said rigid backing members when in contact with the eyelid furrows.

16. The eyelid retracting device of claim 1, wherein said upper and lower arcuate arm portions each further comprising a rigid backing member and a flexible contact face mounted on said rigid backing member; said flexible contact faces each comprising a plurality of flexible riblets;
    wherein said rigid backing members assuming a wishbone shape which approximates the size and configuration of a human eye orbit, said flexible contact faces assuming a wishbone shape which approximates the exposed part of an eyeball, said flexible contact faces reducing their thickness to conform to the size and configuration of the wishbone formed by said rigid backing members when in contact with the eyelid furrows.

17. The eyelid retracting device of claim 16 wherein the flexible contact face and the rigid backing member of a said arm are provided as a two-part injection molded article.

18. The eyelid retracting device of claim 1 wherein the upper and lower arms each include a first recess to receive a facial bone.

19. The eyelid retracting device of claim 1 wherein the upper and lower arm arcuate portions of said upper and lower arms each include a recess which conforms to the eyeball.

20. The eyelid retracting device of claim 1 wherein at least one first end of the upper and lower arms has a texture to facilitate handling of the device.

21. The eyelid retracting device of claim 20 wherein said texture is a roughened surface finish, a brushed finish, a knurled finish, or a molded irregular finish.

22. The eyelid retracting device of claim 1 wherein the first ends of the upper and lower arms include a recess to facilitate handling of the device.

23. The eyelid retracting device of claim 1, wherein said device is made of a material selected from a group consisting of stainless steel, plastic, and molded material.

24. The eyelid retracting device of claim 1, wherein said joint comprises a handle for manipulation of the device, a first end of said handle being operatively associated with said second ends of said arms.

25. The eyelid retracting device of claim 24 wherein said handle further comprises an adjustor to adjust the span between the first ends of said upper and lower arms, said adjustor comprising:
    a built-in nut at the first end of said handle;
    a knob at the second end of said handle to turn the nut;
    a socket at the first end of said handle, to which one end of each said arm is pivotally connected;
    a bolt with one end threading through said socket into the first end of said handle and the other end connected to a connector;
    a first strut with one end pivotally connected to said connector and the other end pivotally connected to a mid-point of said upper arm; and
    a second strut with one end pivotally connected to said connector and the other end pivotally connected to a mid-point of said lower arm.

26. The device of claim 1, wherein the second ends are free ends.

* * * * *